(12) United States Patent
Ramanathan et al.

(10) Patent No.: US 10,562,847 B2
(45) Date of Patent: Feb. 18, 2020

(54) METHOD FOR PREPARATION OF ISOSULFAN BLUE

(71) Applicant: BELOTECA, INC., San Diego, CA (US)

(72) Inventors: Krishna Kumar Ramanathan, Morrisville, NC (US); Bhaskar Rao Venepalli, Cary, NC (US)

(73) Assignee: BELOTECA INVESTMENT FUND 1, LLC, San Diego, CA (US)

( * ) Notice: Subject to any disclaimer, the term of this patent is extended or adjusted under 35 U.S.C. 154(b) by 0 days.

(21) Appl. No.: 16/215,204

(22) Filed: Dec. 10, 2018

(65) Prior Publication Data

US 2019/0152903 A1    May 23, 2019

Related U.S. Application Data

(63) Continuation-in-part of application No. PCT/US2017/037660, filed on Jun. 15, 2017.

(60) Provisional application No. 62/351,018, filed on Jun. 16, 2016.

(51) Int. Cl.
*C07C 303/32* (2006.01)
*C07C 303/06* (2006.01)
*C07C 303/22* (2006.01)
*C07C 309/46* (2006.01)

(52) U.S. Cl.
CPC .......... *C07C 303/32* (2013.01); *C07C 303/06* (2013.01); *C07C 303/22* (2013.01); *C07C 309/46* (2013.01)

(58) Field of Classification Search
None
See application file for complete search history.

(56) References Cited

U.S. PATENT DOCUMENTS

| | | |
|---|---|---|
| 1,531,507 A | 3/1925 | Rosenbaum |
| 1,878,530 A | 9/1932 | Kyrides |
| 2,726,252 A | 12/1955 | Balon et al. |
| 4,330,476 A | 5/1982 | Hermann |
| 4,710,322 A | 12/1987 | Metz |
| 5,659,053 A | 8/1997 | Gessner et al. |
| 6,350,431 B1 | 2/2002 | Snow et al. |
| 7,662,992 B2 | 2/2010 | Kovi et al. |
| 8,969,616 B2 | 3/2015 | Kovi et al. |
| 2002/0022743 A1 | 2/2002 | Pouhov et al. |
| 2008/0281127 A1 | 11/2008 | Kovi et al. |
| 2010/0119447 A1 | 5/2010 | Maloney et al. |

*Primary Examiner* — Ana Z Muresan
(74) *Attorney, Agent, or Firm* — Gendloff IP; Elie Gendloff

(57) ABSTRACT

Provided is a method of preparing isosulfan blue.

17 Claims, No Drawings

METHOD FOR PREPARATION OF ISOSULFAN BLUE

CROSS-REFERENCE TO RELATED APPLICATIONS

This application is a continuation-in-part of PCT Patent Application PCT/US2017/037660, filed Jun. 15, 2017, which claims the benefit of U.S. Provisional Application No. 62/351,018 filed Jun. 16, 2016. Both applications are incorporated by reference herein in its entirety.

BACKGROUND OF THE INVENTION

(1) Field of the Invention

The present application generally relates to methods for preparing pharmaceutical ingredients. More specifically, the application provides improved methods for preparing isosulfan blue.

(2) Description of the Related Art

Isosulfan blue, also known as sulfan blue and patent blue, having the formula

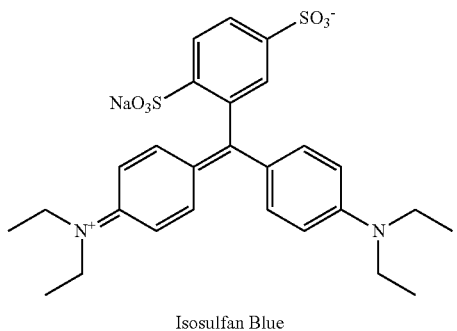

Isosulfan Blue (N-[4-[[4-(diethyl amino) phenyl](2,5-disulfophenyl)methylene]-2,5-cyclohexadien-1-ylidene]-N-ethylethanaminium, sodium salt), is a triarylmethane dye used as contrast agent used in the delineation of lymphatic vessels. As discussed in U.S. Pat. Nos. 7,662,992 and 8,969,616, isosulfan blue is an active pharmaceutical ingredient used in the Lymphazurin™ blue dye, commonly used in a procedure called "mapping of the sentinel lymph nodes". It is an adjunct to lymphography for visualization of the lymphatic system draining the region of injection. An important application is in localizing sentinel lymph nodes in breast cancer patients. Isosulfan blue-guided surgical removal of cancerous tissue is also practiced.

Isosulfan blue is a structural isomer of sulfan blue; both belong to the family of triarylmethane dyestuffs. Generally, preparation of triarylmethane dyes involves condensation of substituted aryl aldehydes with 2 equivalents of alkyl-aryl amines giving rise to leuco-bases or leuco-acids followed by oxidation. Most prior art methods for making of triarylmethane dyes involve strong acids for condensation resulting in leuco-bases or leuco-acids, followed by the use of hazardous oxidizing agents (lead oxide, chloranil, iron phthalocyanine/oxone) for converting to triarylmethane dyes, and crude methods (precipitation with sodium sulfate) of purification. See for example U.S. Pat. Nos. 4,330,476, 4,710,322, 1,531,507, 5,659,053, 1,805,925, 2,422,445, 1,878,530 and 2,726,252. Prior art methods of isolation of the crude leuco-acids or leuco-bases involve tedious neutralization/basification with strong bases and typically using the reaction mixtures in the oxidation step, giving rise to crude triarylmethane dyes. The triarylmethane dyestuffs thus prepared are used mainly for dyeing fabric, coloring paper, and printing inks. The same synthetic and isolation methods are used for the preparation of diagnostically important dyes, such as isosulfan blue, sulfan blue and patent blue V. See, Rodd's Chemistry of Carbon Compounds by S. Coffey, 1974 2nd Edition, Volume III Part F, 110-133.

An alternative procedure is described in U.S. Pat. Nos. 7,662,992 and 8,969,616. In that procedure, 2-chlorobenzaldehyde-5-sulfonic acid, sodium salt is synthesized from 2-chlorobenzaldehyde, then converted to benzaldehyde-2,5-sulfonic acid disodium salt by reacting the 2-chlorobenzaldehyde-5-sulfonic acid with aqueous $Na_2OS_3/NaHSO_3$ under high pressure and temperature. The benzaldehyde-2,5-sulfonic acid disodium salt is then condensed into isoleuco acid, which is reacted with silver oxide to obtain isosulfan blue acid. The isosulfan blue acid is then converted to isosulfan blue by treatment with a sodium solution.

Although that procedure is an improvement from previous procedures for synthesizing isosulfan blue, it still affords significant difficulties. The conversion from isoleuco acid to isosulfan blue acid then isosulfan blue provides significant impurities, and the sodium salts of 2-chlorobenzaldehyde-5-sulfonic acid and benzaldehyde-2,5-sulfonic acid leads to low yields and insoluble inorganic salts. Additionally, the overall yield of isosulfan blue is low—around 26 g isosulfan blue acid per 100 g of 2-chlorobenzaldehyde starting material.

Therefore there is a need in the art for an improved method in the process chemistry of isosulfan blue. The present invention satisfies that need.

BRIEF SUMMARY OF THE INVENTION

Provided is a method of preparing isosulfan blue. The method comprises treating isosulfan blue having formula 5

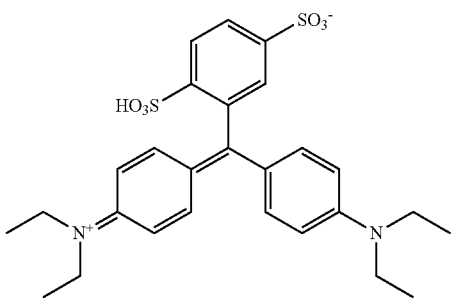

with a sodium ion exchange resin.

Also provided is an additional method of preparing isosulfan blue. This method comprises sulfonation of 2-chlorobenzaldehyde having the formula 1

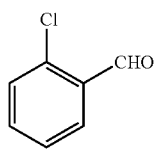

with CaCO₃ and tetra-butylammonium hydroxide in about 30% SO₃ in H₂SO₄ to form 2-chlorobenzaldehyde-5-sulfonic acid tetra-butylammonium salt having the formula 2

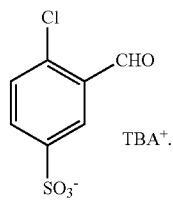

DETAILED DESCRIPTION OF THE INVENTION

As used herein, the singular forms "a", "an" and "the" are intended to include the plural forms as well, unless the context clearly indicates otherwise. Additionally, the use of "or" is intended to include "and/or", unless the context clearly indicates otherwise.

Provided herewith is an improved method for synthesizing isosulfan blue. This improved method provides higher yields and is simpler to carry out than the method described in U.S. Pat. Nos. 7,662,992 and 8,969,616. The overall scheme for various embodiments of this method is:

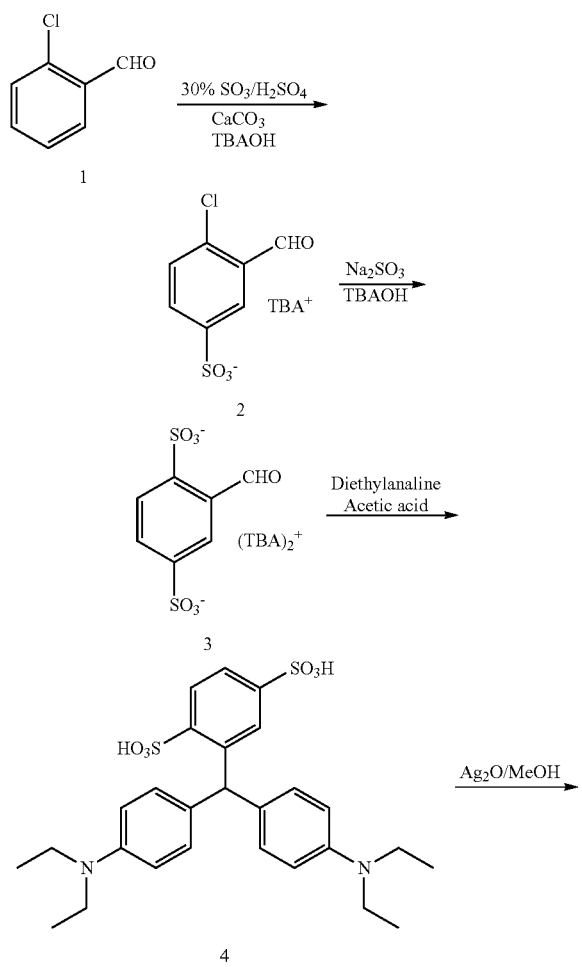

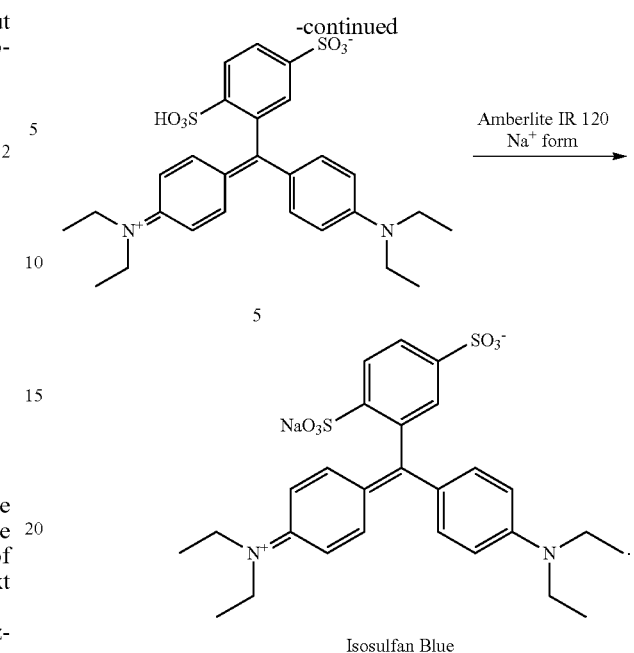

In some embodiments of the present invention, and in accordance with the first step of the above scheme, 2-chlorobenzaldehyde having the formula 1

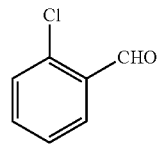

is sulfonated to form 2-chlorobenzaldehyde-5-sulfonic acid tetra-butylammonium salt having formula 2

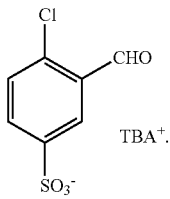

This differs from the procedure described in U.S. Pat. Nos. 7,662,992 and 8,969,616 in that the tetra-butylammonium (TBA) salt, rather than the sodium salt, of 2-chlorobenzaldehyde-5-sulfonic acid is prepared. This is an improvement over that procedure since the TBA salt of the intermediates 2 and 3 (below) can be easily extracted into organic solvents, so the reactions are simple to work with. The sodium salt of 3 is insoluble in organic solvents, making it extremely difficult to purify and resulting in low yields.

This sulfonation reaction can be by any procedure known in the art. In some embodiments, 2-chlorobenzaldehyde is reacted with CaCO₃ and tetra-butylammonium hydroxide in about 30% SO₃ in H₂SO₄.

In some embodiments and as illustrated as the next step of the above scheme, nucleophilic displacement of the chloride of 2-chlorobenzaldehyde-5-sulfonic acid tetra-butylammonium salt is carried out to obtain benzaldehyde-2,5-sulfonic acid tetra-butylammonium salt having formula 3

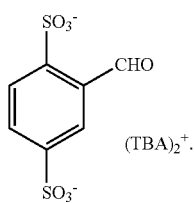

3

This may be carried out by any procedure known in the art. In some embodiments, the 2-chlorobenzaldehyde-5-sulfonic acid tetra-butylammonium salt is reacted with $Na_2SO_3$ and tetra-butylammonium hydroxide, for example in refluxing water and ambient pressure for 18-24 hours.

In various embodiments of the invention and as illustrated as the next step of the above scheme, the benzaldehyde-2,5-sulfonic acid tetra-butylammonium salt is condensed with diethylaniline in acetic acid in to provide isoleuco acid having formula 4

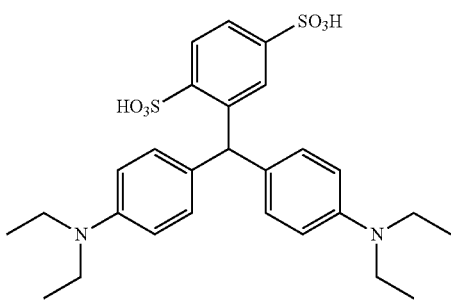

4

The condensation can be achieved by any means known in the art. In some embodiments, the benzaldehyde-2,5-sulfonic acid tetra-butylammonium salt is refluxed with diethylaniline in acetic acid. In various embodiments, this procedure is executed in an oxygen-free system, e.g., in a nitrogen atmosphere.

In further embodiments of the invention and as illustrated as the next step of the above scheme, the isoleuco acid is suspended in a polar solvent with a metallic oxide, recovering isosulfan blue acid having formula 5

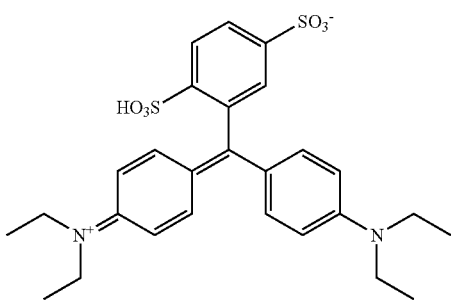

5

This step can be performed by any means known in the art. Any metallic oxide may be used in this step. In some embodiments, the metallic oxide is silver oxide or manganese oxide. In various embodiments of this step, the polar solvent is methanol. In additional embodiments, this reaction is performed in an oxygen-free system, for example a nitrogen atmosphere. In various embodiments, the reaction is performed in the dark. The inert oxygen-free system is useful for minimizing the formation of impurities.

In additional embodiments of the invention and as illustrated as the next step of the above scheme, the isosulfan blue acid is converted to isosulfan blue, having the following formula

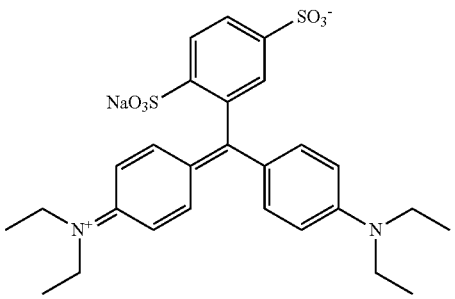

Isosulfan Blue

The conversion from isosulfan blue acid to isosulfan blue can be by any means known in the art. In some embodiments, the conversion is carried out by treating the isosulfan blue acid with a sodium solution, for example as described in U.S. Pat. No. 8,969,616. In other embodiments, the isosulfan blue acid is treated with a sodium ion exchange resin, e.g., Amberlite IR 120 $Na^+$. This use of a sodium ion exchange resin is a simpler procedure than the treatment with a sodium solution as described in U.S. Pat. No. 8,969,616.

The scheme illustrated above provides isosulfan blue having purity of about 99% by HPLC, avoiding any significant amounts of various impurities such as isosulfan blue acid (compound 5 above), isoleuco acid (compound 4 above), 2-chlorobenzaldehyde (compound 1 above), the diethylamino-ethylamino analog of isosulfan blue, having formula 6

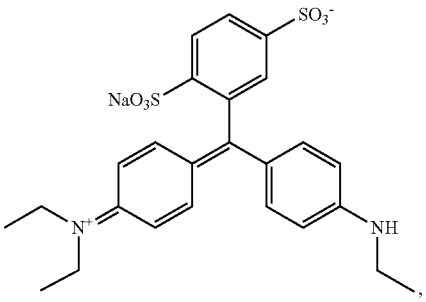

6 the bis(ethylamino) analog of isosulfan blue, having formula 7

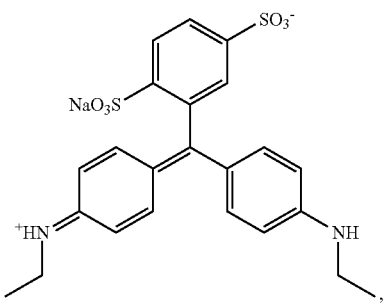

the diethylamino-amino analog of isosulfan blue, having formula 8

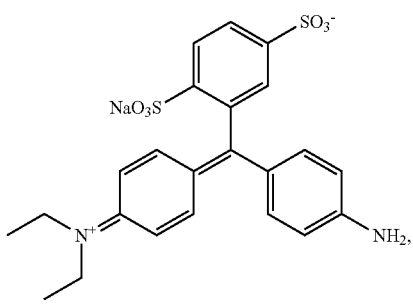

and N,N-diethylaniline, having formula 9

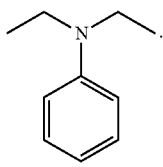

The yield using the above scheme is about 162 g isosulfan blue acid per 100 g of 2-chlorobenzaldehyde starting material. This compares favorably to the yield of the procedure described in U.S. Pat. No. 8,969,616, which is about 26 g isosulfan blue acid per 100 g of 2-chlorobenzaldehyde.

This isosulfan blue preparation can be further purified using any method known in the art, e.g., batch or column chromatography, for example normal phase chromatography (e.g., silica gel), reverse phase chromatography (e.g., C18), ion exchange chromatography (e.g., anion or cation), size exclusion chromatography, etc.

Preferred embodiments are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

Example 1. Preparation of Isosulfan Blue from Benzaldehyde-2,5-sulfonic Acid Tetra-Butylammonium Salt Benzaldehyde-2,5-sulfonic acid tetra-butylammonium salt (compound 3) and acetic acid were charged to a clean, nitrogen flushed 5-liter 4-neck reaction flask equipped with overhead stirrer, nitrogen inlet, an addition funnel, a reflux condenser and heating mantle. The heating was regulated through a Variac. The mixture was bubbled with nitrogen for 30 minutes to expel any residual oxygen present in the system. To this reaction mixture, diethylaniline (compound 9), bubbled with nitrogen for 20 min, was added and the contents were heated at reflux temperature for 16±5 hours. The reaction mixture was cooled to room temperature and filtered through a Buchner funnel. The off-white precipitate was washed with a mixture of MeOH/DCM (1:1, 500±100 mL).

After methanol stopped dripping from the funnel, the crude product was transferred to a 5-L 4-neck reaction flask fitted with a nitrogen inlet. Methanol (3400±200 mL) and silver oxide were added under an atmosphere of nitrogen. The reaction flask was covered with aluminum foil and stirred at room temperature for 18±6 hours. The dark blue mixture was filtered through a sintered glass flask and rinsed with methanol (500±100 mL). The solid was transferred back into the reaction flask and stirred with methanol (1500±200 mL) for 20 minutes and filtered again. The solid was rinsed with methanol (500±100 mL) and this process of stirring in methanol and filtering repeated until the color of the filtrate became light blue. The filtrate was transferred to a 10 liter round bottom flask and concentrated in vacuo in a rotary evaporator. After removal of methanol, the solid was stirred with acetone (800±200 mL) for 20±10 minutes. The solid was filtered and washed with acetone.

The solid was dissolved in water (1000±200 mL) and Amberlite IR 120 Na+ form resin (300±50 mL) was added and stirred well. This mixture was poured on top of a bed of the same resin (900±100 mL) in a sintered glass funnel and eluted with water. To this filtrate, ISOLUTE Si-Thiol was added and stirred for 3 hours. The suspension was filtered and water was removed in a rotary evaporator to obtain isosulfan blue. The material was dried in vacuo in a rotary evaporator at 45±5° C. to constant weight.

Purity of the final material was about 99% isosulfan blue, as determined by HPLC.

The above procedures were performed by Krishna Kumar Ramanathan and Bhaskar Rao Venepalli at CiVentiChem, 1001 Sheldon Drive, Cary, N.C. 27513.

In view of the above, it will be seen that several objectives of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A method of preparing N-[4-[[4-(diethyl amino) phenyl](2,5-disulfophenyl)methylene]-2,5-cyclohexadien-1-ylidene]-N-ethylethanaminium, sodium salt (isosulfan blue)

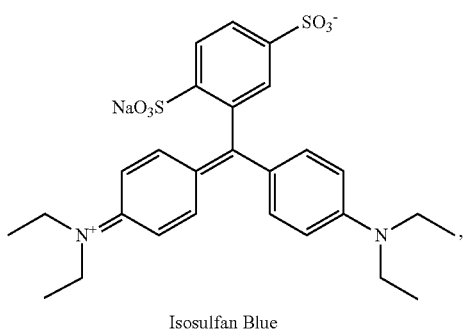

Isosulfan Blue the method comprising treating isosulfan blue acid having formula 5

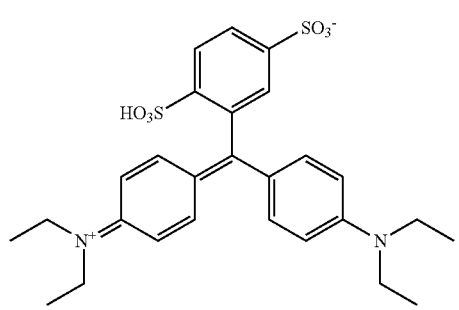

with a sodium ion exchange resin.

2. The method of claim 1, further comprising combining a suspension of isoleuco acid having formula 4

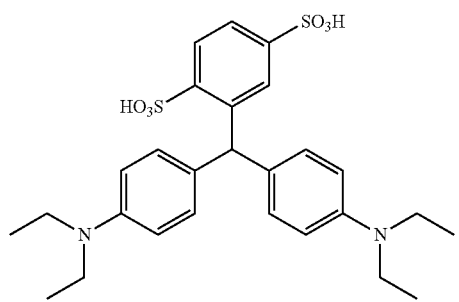

in a polar solvent with a metallic oxide, recovering isosulfan blue acid.

3. The method of claim 2, wherein the polar solvent is methanol.

4. The method of claim 1, further comprising sulfonation of 2-chlorobenzaldehyde having the formula 1

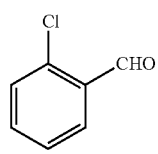

with $CaCO_3$ and tetra-butylammonium hydroxide in about 30% $SO_3$ in $H_2SO_4$ to form 2-chlorobenzaldehyde-5-sulfonic acid tetra-butylammonium salt having the formula 2

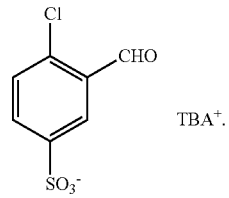

5. The method of claim 4, further comprising nucleophilic displacement of the chloride of 2-chlorobenzaldehyde-5-sulfonic acid tetra-butylammonium salt to obtain benzaldehyde-2,5-sulfonic acid tetra-butylammonium salt having formula 3

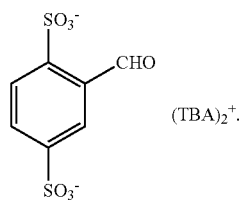

6. The method of claim 5, wherein the 2-chlorobenzaldehyde-5-sulfonic acid tetra-butylammonium salt is reacted with $Na_2SO_3$ and tetra-butylammonium hydroxide.

7. The method of claim 5, wherein the benzaldehyde-2,5-sulfonic acid tetra-butylammonium salt is condensed with diethylaniline in refluxing acetic acid in to provide isoleuco acid having formula 4.

8. The method of claim 1, wherein the isosulfan blue is treated with a silica-bonded 1-propanethiol after treatment with the sodium ion exchange resin.

9. A method of preparing N-[4-[[4-(diethyl amino) phenyl](2,5-disulfophenyl)methylene]-2,5-cyclohexadien-1-ylidene]-N-ethylethanaminium, sodium salt (isosulfan blue)

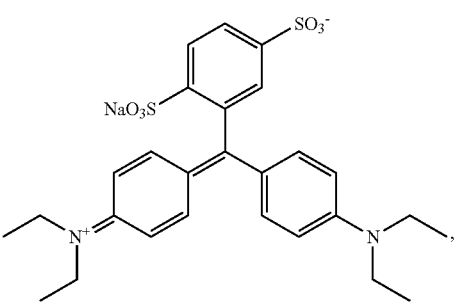

Isosulfan Blue the method
comprising sulfonation of 2-chlorobenzaldehyde having the formula 1

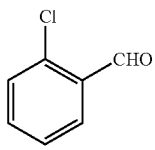

with CaCO₃ and tetra-butylammonium hydroxide in about 30% SO₃ in H₂SO₄ to form 2-chlorobenzaldehyde-5-sulfonic acid tetra-butylammonium salt having the formula 2

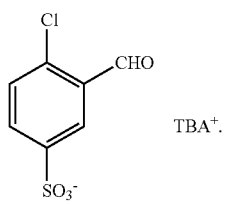

10. The method of claim 9, further comprising nucleophilic displacement of the chloride of 2-chlorobenzaldehyde-5-sulfonic acid tetra-butylammonium salt to obtain benzaldehyde-2,5-sulfonic acid tetra-butylammonium salt having formula 3

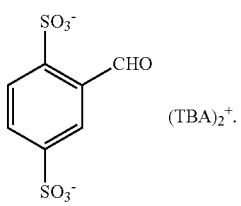

11. The method of claim 10, wherein the 2-chlorobenzaldehyde-5-sulfonic acid tetra-butylammonium salt is reacted with Na₂SO₃ and tetra-butylammonium hydroxide.

12. The method of claim 10, wherein the benzaldehyde-2,5-sulfonic acid tetra-butylammonium salt is condensed with diethylaniline in refluxing acetic acid in to provide isoleuco acid having formula 4

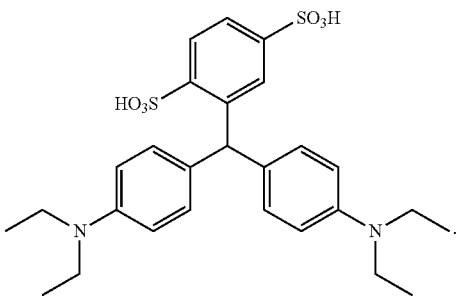

13. The method of claim 12, further comprising combining a suspension of isoleuco acid in a polar solvent with a metallic oxide, recovering isosulfan blue acid having formula 5

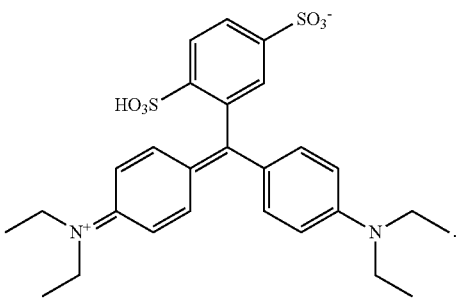

14. The method of claim 13, wherein the polar solvent is methanol.

15. The method of claim 9, further comprising treating isosulfan blue acid with a sodium ion exchange resin to form isosulfan blue.

16. The method of claim 2, wherein the metallic oxide is silver oxide or manganese oxide.

17. The method of claim 13, wherein the metallic oxide is silver oxide or manganese oxide.

\* \* \* \* \*